(12) United States Patent
Ibeanusi et al.

(10) Patent No.: US 12,017,930 B1
(45) Date of Patent: Jun. 25, 2024

(54) ELECTROMAGNETICS-ASSISTED NUTRITIONAL ENHANCEMENT OF ALGAL SILAGE FOR AQUACULTURE

(71) Applicant: Florida A&M University, Tallahassee, FL (US)

(72) Inventors: Victor Madu Ibeanusi, Ellenwood, GA (US); Satyanarayan Dev, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 702 days.

(21) Appl. No.: 17/086,971

(22) Filed: Nov. 2, 2020

Related U.S. Application Data

(60) Provisional application No. 62/928,514, filed on Oct. 31, 2019.

(51) Int. Cl.
  *C02F 1/30* (2023.01)
  *C12M 1/00* (2006.01)
  *C12M 1/42* (2006.01)
  *C12N 13/00* (2006.01)
  *A01G 33/00* (2006.01)

(52) U.S. Cl.
  CPC ............ *C02F 1/302* (2013.01); *C12M 21/02* (2013.01); *C12M 35/02* (2013.01); *C12N 13/00* (2013.01); *A01G 33/00* (2013.01)

(58) Field of Classification Search
  CPC . C02F 3/32; C02F 1/30; C12M 21/02; C12M 35/02; C12M 13/00
  See application file for complete search history.

(56) References Cited

U.S. PATENT DOCUMENTS

| | | | | |
|---|---|---|---|---|
| 6,008,028 A | * | 12/1999 | Bender | C12N 1/20 210/150 |
| 8,569,050 B1 | * | 10/2013 | Ericsson | C12M 21/02 435/292.1 |

FOREIGN PATENT DOCUMENTS

CN            101479887 A  *  7/2009  ............. H01Q 13/00

OTHER PUBLICATIONS

Translation of CN-101479887-A (Year: 2009).*

* cited by examiner

*Primary Examiner* — Walter D. Griffin
*Assistant Examiner* — Cameron J Allen
(74) *Attorney, Agent, or Firm* — Owen G. Behrens; Smith & Hopen, P.A.

(57) ABSTRACT

Methods and related devices for enhancing the nutritional value of algal silage for aquaculture using electromagnetic radiation to expedite and make uniform the annealing process of the microalgae on the silage. New isolates have been screened for their natural abilities to produce added nutritional value comparable, if not higher, relative to industry gold standard strains.

18 Claims, 6 Drawing Sheets

ELECTROMAGNETICS-ASSISTED NUTRITIONAL ENHANCEMENT OF ALGAL SILAGE FOR AQUACULTURE

CROSS-REFERENCE TO RELATED APPLICATIONS

This nonprovisional application is a continuation of and claims priority to provisional application No. 62/928,514, entitled "ELECTROMAGNETICS-ASSISTED NUTRITIONAL ENHANCEMENT OF ALGAL SILAGE FOR AQUACULTURE," filed Oct. 31, 2019 by the same inventors.

BACKGROUND OF THE INVENTION

1. Field of the Invention

This invention generally relates to the nutritional enhancement of microalgal silage (e.g., algal silage) for aquaculture. More specifically, it relates to the nutritional enhancement of algal silage for aquaculture using electromagnetics to improve the annealing process.

2. Brief Description of the Prior Art

Aquaculture (i.e., the breeding, rearing, and harvesting of marine animals and other organisms in various water environments) is critical to resolving the world's food insecurity and projected future food shortages. According to studies, food production likely needs to double by 2050 to feed the projected world population of roughly 9.2 billion, up from 7.6 billion in 2018. In response to the projected food shortages, the world's oceans represent the greatest potential protein source. Specifically, the world's oceans can generate 30× more yield per acre of water versus an acre of land.

The federal government recognizes the importance of growing the aquaculture industry. The National Oceanic and Atmospheric Administration (NOAA) has stated that marine aquaculture is an integral part of its strategy for building economic and environmental resiliency in coastal communities. Aquaculture will be an ever-growing portion of the seafood industry, providing accessible, affordable seafood while bringing much needed economic development.

For example, the ocean ecosystem depends upon a vibrant oyster population. An individual oyster can filter up to 50 gallons of water a day. The high filtering rate of oysters significantly improves the surrounding water quality. Furthermore, it sets into motion the nutrient stream that underpins the entire food chain. However, a decreasing fishmeal supply is a significant concern for the aquaculture industry's future—particularly for the oyster population's health. Fishmeal is a high protein feed ingredient used in almost all intensive aquaculture systems. It is derived mainly from the bones and offal (e.g., organ meats) leftover from commercial fisheries by-catch.

The use of algal silage as a dietary replacement for fishmeal is a solution proposed by many researchers. Preparing algal silage from microalgae has several advantages. For example, the algal biomass resources are converted into dietary materials for aquacultured aquatic life. Moreover, the algal silage is acidic, which leads to a long shelf life even when stored at room temperature. Thus, a surplus of cultured algal silage can be preserved and later utilized depending on demand. In periods of high demand, the algal silage is then distributed to other aquaculture farms worldwide. Furthermore, the microalgal silage also provides several health benefits for aquacultured organisms and results in high-quality cultured fish and shellfish-including oysters. Additionally, the algal silage microbial mat protects and feeds the aquatic life below the aquaculture system's microbial mat.

Accordingly, what is needed is the improvement of algal silage production, such as by using metagenomic techniques to incorporate new algae and bacterial prospects, thereby enhancing the nutritional value for high-yield aquaculture using electromagnetic radiation to improve the annealing process. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies, and the definition of that term in the reference does not apply.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act, or item of knowledge is referred to or discussed, this reference or discussion is not an admission that the document, act, or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for improving the nutritional properties of microbial mats using electromagnetic radiation is now met by a new, useful, and nonobvious invention.

The novel structure includes a device for supply a dose of electromagnetic radiation to a microbial mat. The device includes an annealing area. An electromagnetic radiation generator is configured to supply the dose of electromagnetic radiation that is supplied by the electromagnetic radiation generator to the annealing area. In an embodiment, the electromagnetic radiation generator is selected from the group consisting of a 2.45 GHz microwave generator, a magnetron, and a solid-state pulse generator. The device may further include a power control mechanism configured to adjust one or more variables of the dose of electromagnetic radiation emitted from the electromagnetic radiation generator. In an embodiment, the electromagnetic radiation is microwave or radio-frequency radiation. Additionally, the device may further include a tuner, such as a manual three-stub tuner, that is adapted to adjust the reflected power of the device.

The novel method includes a method of enhancing a nutritional quality of algal silage. The method includes a step of capturing an amount of algal-microbial biomass and an amount of wastewater. The amount of algal-microbial biomass and the amount of wastewater are disposed within a bioreactor. The method includes a step of subjecting the amount of algal-microbial biomass and the amount of wastewater to electromagnetic radiation emitted from an electromagnetic generator via a slotted waveguide. The electromagnetic radiation may be microwave energy, radiofrequency energy, or other similar uniformly-distributing radiation sources. In an embodiment, a plurality of doses of electromagnetic radiation are emitted from the electromagnetic generator. In an embodiment, the plurality of doses of electromagnetic radiation are emitted for approximately two hours per day for a period of between three and five days.

Via the electromagnetic radiation, the amount of algal-microbial biomass and the amount of water are uniformly heated to a predetermined temperature, thereby converting at least a portion of the amount of algal-microbial biomass and the amount of wastewater into a microbial mat. The predetermined temperature is a temperature at which microorganism growth within the amount of algal-microbial biomass is inhibited. In an embodiment, the predetermined temperature varies by less than approximately 12.5% across the microbial mat. Once formed and annealed, the microbial mat is disposed on a surface of a body of water, such that the microbial mat is configured to serve as a feed source for aquaculture organisms disposed beneath the surface of the body of water.

In an embodiment, the slotted waveguide is a non-linear slotted waveguide. In such an embodiment, the method includes a step of concentrating an amount of the electromagnetic radiation via an annealing area of the non-linear slotted waveguide in a direction toward the bioreactor.

These and other important objects, advantages, and features of the invention will become clear as this disclosure proceeds.

The invention accordingly comprises the features of construction, combination of elements, and arrangement of parts that will be exemplified in the disclosure set forth hereinafter, and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a newly developed solid-state microwave applicator used to improve the nutritional composition of microalgae on algal silage (i.e., a microbial mat) and expedite the annealing process of the microalgae of a microbial mat. Furthermore, new isolates have been screened for their abilities to produce added nutritional value that is greater than or equal to relative to industry gold standard strains. For example, approximately 100 different isolates have been screened for providing enhanced nutritional value, including: *Aequorivita, Aeromicrobium, Agarivorans, Agrococcus, Algibacter, Algicola, Algoriphagus, Aquimarina, Aureispira, Brevibacterium, Brevundimonas, Cellulophaga, Croceitalea, Demequina, Dinoroseobacter, Erythrobacter, Ferrimonas, Flavobacterium, Formosa, Fucobacter, Halolactibacillus, Hoeflea, Kiloniella, Koreibacter, Kriegella, Labedella, Lacinutrix, Lentibacter, Leuconostoc, Leucothrix, Luteolibacter, Maribacter, Marinobacter, Marinovum, Maritalea, Marivita, Mesonia, Microbulbifer, Nitratireductor, Oceanicaulis, Oceanobacillus, Paracoccus, Paraliobacillus, Phycicoccus, Phycicola, Planktotalea, Pseudoalteromonas, Pseudomonas, Pseudozobellia, Roseibacillus, Roseibium, Roseivirga, Roseovarius, Salinicoccus, Shewanella, Tenacibaculum, Ulvibacter, Vampirovibrio, Winogradskyella,* and *Zobellia*.

Figure 1:
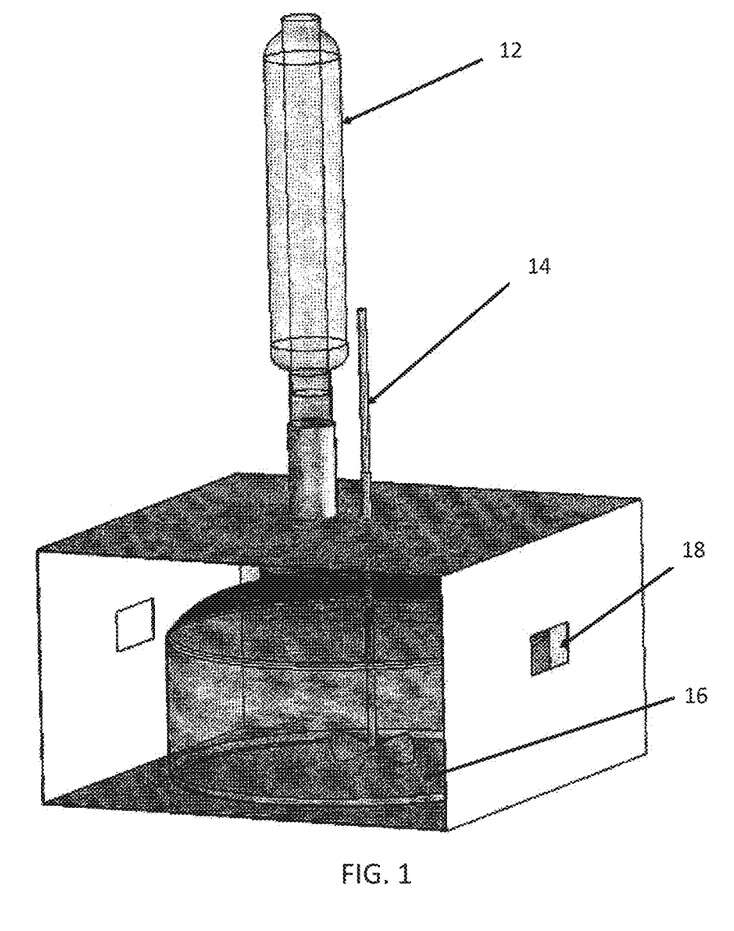
FIG. 1 is a perspective view depicting an embodiment of a microbial mat bioreactor, in accordance with an embodiment of the present invention.

FIG. 1 depicts an embodiment of a microbial mat bioreactor system, including a bioreactor within which the biological reaction to create the microbial mat takes place. The bioreactor system includes microbial mat bioreactor 16 (alternatively referred to as bioreactor 16) that is in communication with wastewater inflow 12. Wastewater inflow 12 provides nutrients necessary for the creation of a microbial mat within microbial mat bioreactor 16, such that microbial growth (i.e., algal and bacterial growth) is stimulated within bioreactor 16. At least one exterior wall of the bioreactor system includes an aperture that functions as microwave port 18 in use, which will be described in further detail below. In addition, impeller shaft 14 is disposed through an exterior wall of bioreactor 16, such that, during use, impeller shaft 14 mixes material disposed within bioreactor 16.

Figure 2:
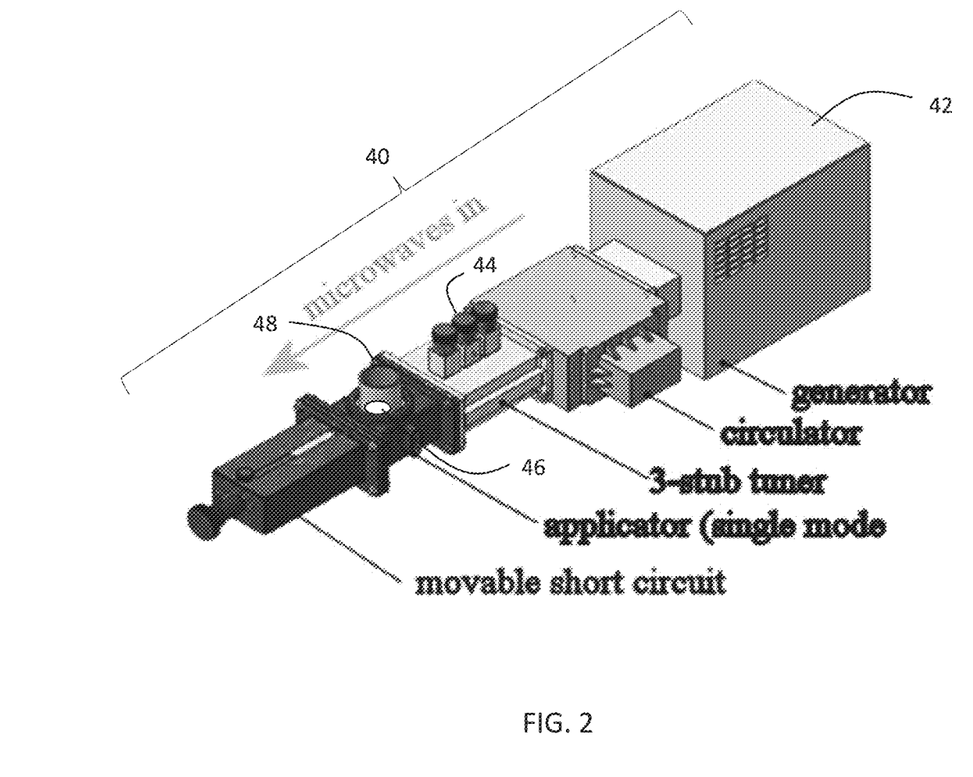
FIG. 2 is a perspective view depicting an embodiment of a microwave energy applicator in the form of a focused single-mode microwave device, the applicator used in combination with the microbial mat bioreactor of FIG. 1.

FIG. 2 depicts an embodiment of electromagnetic radiation device 40 used in combination with the bioreactor system shown in FIG. 1. Electromagnetic radiation device 40 includes microwave generator 42, power controller 44, and waveguide applicator 46. In use, microwave generator 42 is configured to emit radiation, such as microwave energy or radiofrequency (RF) energy. The radiation generated via microwave generator 42 exits electromagnetic radiation device 40 via waveguide applicator 46.

The portion of electromagnetic radiation device 40 that includes waveguide applicator 46 may be referred to as annealing area 48, since it is used in an annealing process in combination with the microbial mat bioreactor system depicts in FIG. 1. In addition, electromagnetic radiation device 40 includes power controller 44 that is in electric communication with microwave generator 42. Via power controller 44, a user can customize a level of microwave energy traveling through electromagnetic radiation device 40 and emitted via waveguide applicator 46. Waveguide applicator 46 is in mechanical communication with the microbial mat bioreactor system via microwave port 18. As such, electromagnetic radiation device 40 is configured to emit energy in a direction toward microbial mat bioreactor 16 to subject bioreactor 16 to microwave energy, as will be discussed in detail below.

Figure 3A:
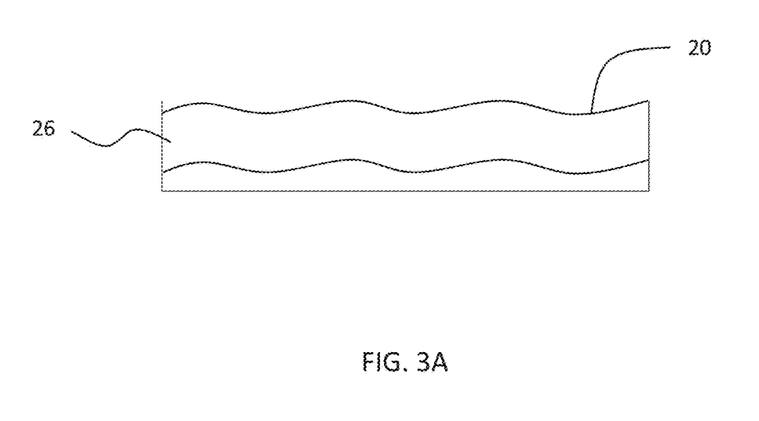
FIG. 3A is an orthogonal view of a microbial mat disposed on a surface of a body of water, in accordance with an embodiment of the present invention.
Figure 3B:
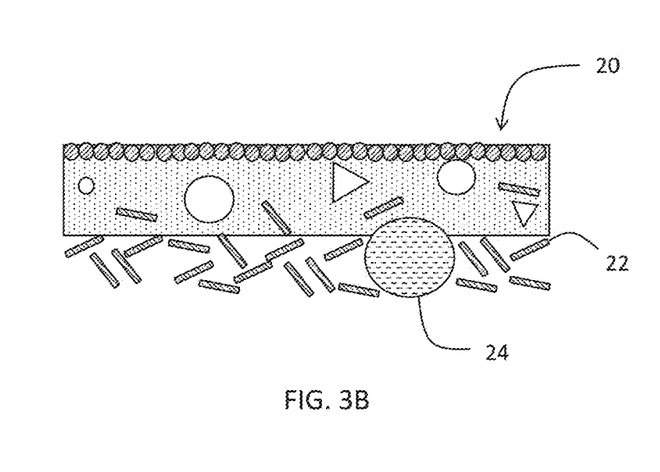
FIG. 3B is a close-up orthogonal view of the microbial mat of FIG. 3A.

FIGS. 3A-3B depict an embodiment of microbial mat 20 (also referred to as algal silage) created via the bioreactor system depicted in FIG. 1 and electromagnetic radiation device 40 depicted in FIG. 2. In particular, FIG. 3A depicts microbial mat 20 as a floating structure on the surface of a body of water, such as wastewater 26. Microbial mat 20 contains algal-microbial biomass and is produced using wastewater 26 and an annealing process. Microbial mats 20 are layered communities of microorganisms 22 typically only a few millimeters thick, as shown in particular in FIG. 3B. Microorganisms 22 of microbial mat 20, as well as gas pocket 24, conduct several biogeochemical processes. For example, microbial mats 20 perform photosynthesis, respiration, and acquire nitrogen through nitrogen fixation. Thus, microbial mats 20 create a fully functioning and self-sustaining ecosystem containing organic carbon producers and consumers. Microbial mats 20 are self-organized laminated structures that have been annealed tightly together by the slimy secretions from the various microorganisms 22 that are part of microbial mat's 20 ecosystem.

Figure 4:
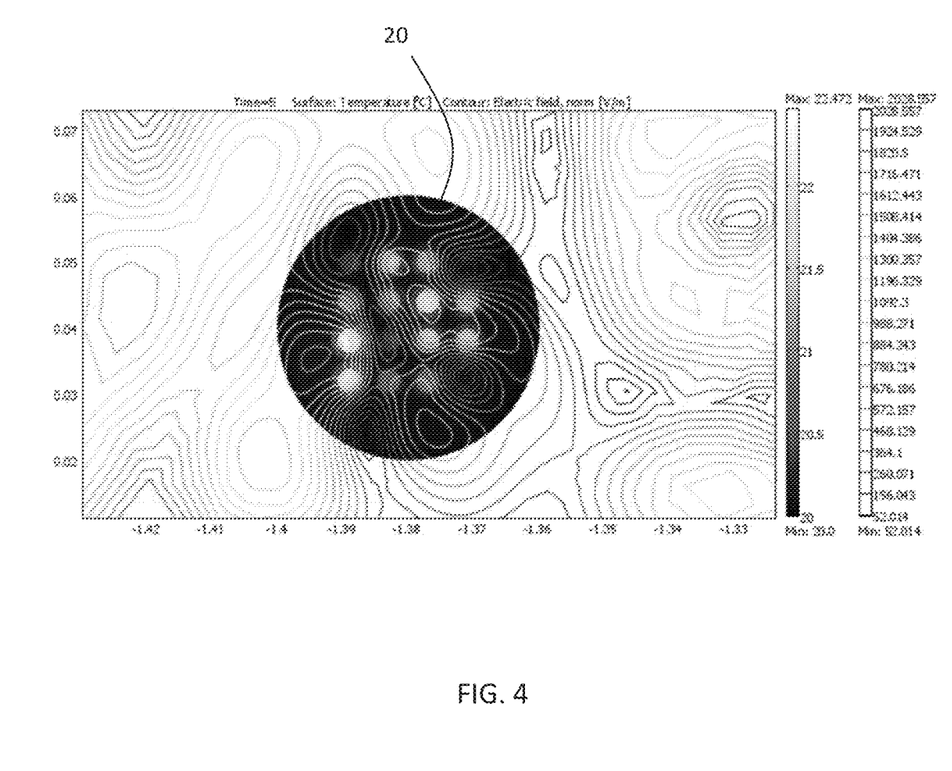
FIG. 4 is a graphical depiction of uniform heat distribution across a microbial mat, in accordance with an embodiment of the present invention.

While examples of microbial mats, including naturally-occurring microbial mats, exist within the prior art, such mats fail to adequately and consistently create a functioning and self-sustaining ecosystem within the surrounding environment. As such, an improved microbial mat 20 is created by way of an improved annealing process utilizing electromagnetic radiation, such as microwave and radiofrequency (RF) energy. During the annealing process, microbial mat 20 is heated to predetermined temperatures to inhibit or inactivate microorganism 22 growth. These predetermined temperatures for the purpose of the annealing process vary depending on the particular composition of microorganisms 22 comprising microbial mat 20. However, importantly, electromagnetic radiation is utilized to accomplish the volumetric heating of annealing process by heating microorganisms 22 to the predetermined temperature. The use of electromagnetic radiation, as opposed to other forms of heating, ensures that uniform distribution of temperatures about microbial mat 20 is accomplished. Moreover, the use of electromagnetic radiation ensures a near-instantaneous heating process for microorganisms 22, thereby efficiently and effectively annealing microbial mat 20 in a uniform manner. An example of the uniform temperature and electric field distributions for microbial mat 20 is shown in FIG. 4, which depicts a narrow range of approximately 20° C. to approximately 22.5° C. across microbial mat 20, showing the uniform heating accomplished during the annealing process for microbial mat 20.

As mentioned above, the annealing of microbial mats 20 is accomplished efficiently and effectively using one or more doses of electromagnetic radiation. Such electromagnetic radiation is generated by electromagnetic generator 42, such as the 2.45 GHz microwave generation system depicted in FIG. 2. However, it is appreciated that the annealing of microbial mat 20 may be accomplished by other means, such as through the use of a solid-state pulse generator (SSPG), to generate microwave power or microwave radiation.

In an embodiment, waveguide applicator 46 optimally distributes the microwave energy in annealing area 48 to microbial mat 20. Specifically, non-linear slotted waveguide applicator 46 uniformly distributes the microwave radiation to microbial mat 20 to accomplish ideal annealing conditions. Regardless of the application method, non-linear slotted waveguide applicator 46 does not interfere with microbial mat's 20 integrity, formation, or growth during the application of the electromagnetic radiation when performing the annealing process.

Overall, by improving the annealing process, microbial mat's 20 integrity and strength are significantly improved, leading to an increase in the nutritional value of microbial mat 20. Thus, the overall production and/or synthesis of various macro and micronutrients beneficial for increasing microbial mat's nutritional 20 value for aquacultured organisms is significantly improved using electromagnetic energy, such as microwave energy.

Figure 5A:
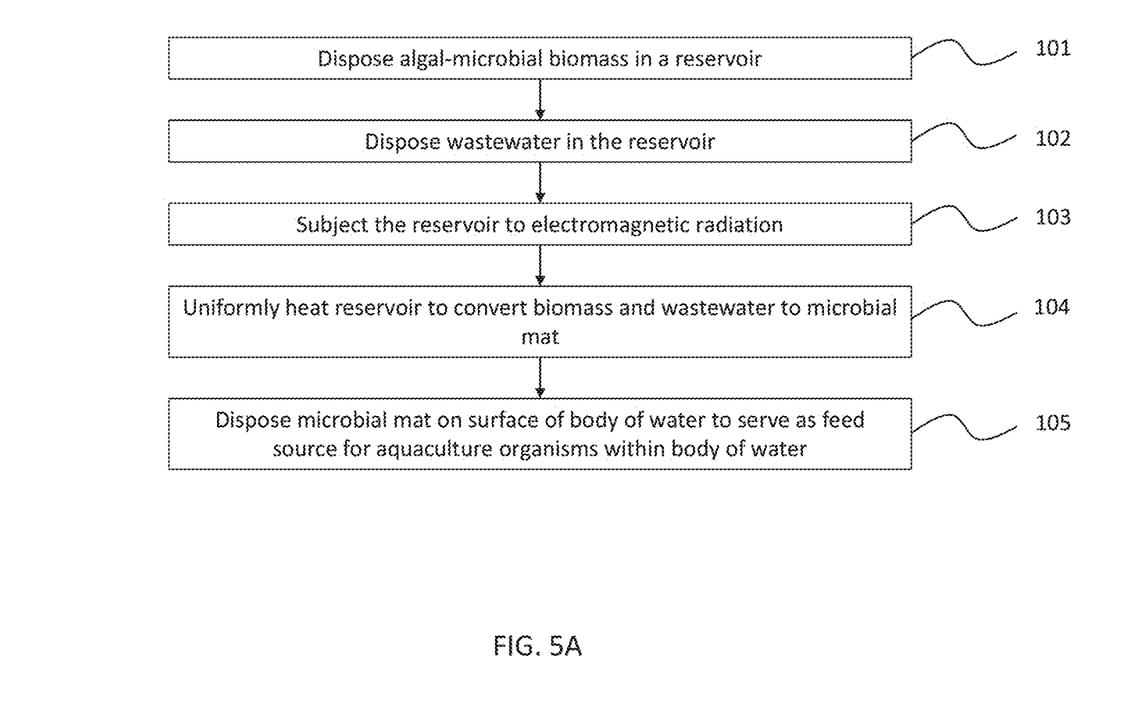
FIG. 5A is a process flow diagram depicting a method of creating a microbial mat, in accordance with an embodiment of the present invention.
Figure 5B:
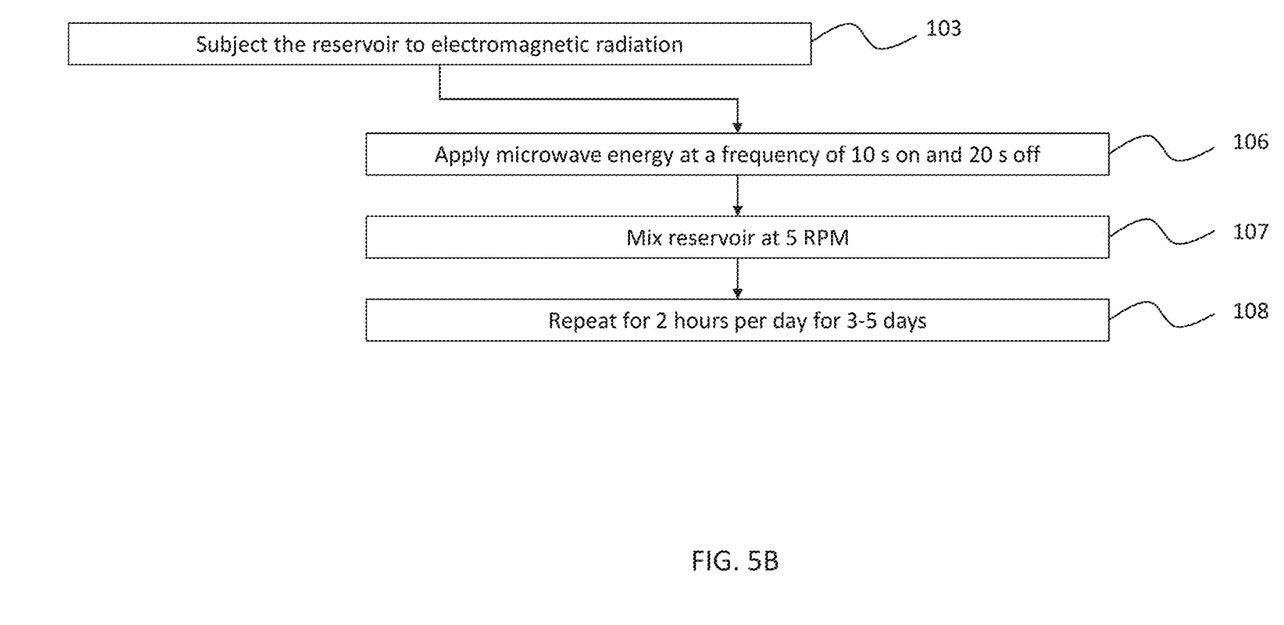
FIG. 5B is a process flow diagram depicting a method of subjecting a bioreactor to electromagnetic radiation to create a microbial mat, in accordance with an embodiment of the present invention.

Referring now to FIGS. 5A-5B, in conjunction with FIGS. 1-4, exemplary process flow diagrams are provided, depicting methods of producing a source of feed for aquacultured organisms. The steps delineated in the exemplary process flow diagrams of FIGS. 5A-5B are merely exemplary of a preferred order for the method of producing a source of feed for aquacultured organisms. The steps may be carried out in another order, with or without additional steps included therein. Additionally, the steps may be carried out with an alternative embodiment of non-slotted waveguide device 40, as contemplated in the description above.

The method for producing a stable and nutritional source of feed for aquacultured organisms begins at step 101, which includes disposing an amount of algal-microbial biomass within a reservoir (referred to as a bioreactor hereinafter), such as the bioreactor 16. In addition, during step 102, an amount of wastewater is disposed within the bioreactor. In an embodiment, each of steps 101 and 102 are performed together by disposing wastewater within the bioreactor, with the algal-microbial biomass being derived from the wastewater. To prepare the bioreactor for a bio-chemical reaction to generate a microbial mat, such as microbial mat 20, the bioreactor receives a layer of plaster, wood shavings, paper, and other similar materials. The layer is sized to cover only the bottom surface of the bioreactor. In an embodiment, an amount of soil is disposed within the bioreactor as well—for example, approximately one inch of soil can be disposed atop the bottom layer of the bioreactor. An approximately equal amount of water is then disposed on the soil. In an embodiment, an amount of light, such as sunlight or light-emitting diode (LED) light is directed into the bioreactor. The LED light is within the wavelength range of 600-700 nm. As such, the bioreactor is prepared for a bio-chemical reaction to generate a microbial mat.

During step 103, the bioreactor is subjected to electromagnetic radiation. As discussed above, the electromagnetic radiation can be provided via waveguide device 40, specifically via microwave generator 42 and waveguide applicator 28. For example, non-linear slotted waveguide device 40 is provided for distributing a dose of electromagnetic radiation to microbial mat 20. Microbial mat 20 receives the dose of electromagnetic radiation generated by electromagnetic radiation generator 42 and applied to microbial mat 20 using non-linear slotted waveguide applicator 46. In an embodiment (shown in FIG. 5B), microwave energy from a solid-state pulse generator is applied to the bioreactor with a pulse on frequency of approximately 10 seconds, and a pulse off frequency of approximately 20 seconds during step 106. The bioreactor is mixed at approximately 5 RPM, such as via impeller shaft 14, during step 107. During step 108, this process repeats for approximately 2 hours per day for a period of 3-5 days, thereby producing algal biomass as a microbial mat similar to the results obtained in 4 weeks without the microwave applications. As such, the methods described herein dramatically improve the efficiencies associated with producing microbial mats via the synergistic relationship between the materials within the bioreactor and the electromagnetic energy to which the bioreactor is subjected.

Returning to FIG. 5A., during step 104, the dose of electromagnetic radiation distributed to microbial mat 20 uniformly heats microbial mat 20 to a predetermined temperature. The predetermined temperature inhibits microorganism growth within microbial mat 20, thereby permitting microbial mat 20 to serve as a feed source for aquacultured organisms. Finally, during step 105, the microbial mat is disposed on a surface of a body of water to serve as a feed source for aquacultured organisms within the body of water, benefitting from the efficient method that reducing production time by approximately 75%.

EXAMPLE

In a photosynthetic microbial mat, the photosynthetic activity of the cyanobacteria creates an oxygenated environment in the upper layer of the mat. In moist conditions, mats are usually held together by slimy substances secreted by the microorganisms. In many cases, some of the bacteria form tangled webs of filaments which make the microbial mat tougher. The best-known physical forms are flat mats and stubby pillars called stromatolites, but there are also spherical forms.

Among the different species in the microbial mat, the thermophilic bacteria secrete more slimy substances in a shorter time. Also, the slimy secretions of the algae increase with increased temperature exposures. In this particular case, the fluctuating temperature conditions created by the electromagnetic radiation discussed above, as well as the volumetric molecular heat generation phenomenon inherent to electromagnetic radiation heating, result in both enhanced secretions as well as filament formation in the bacteria.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of enhancing a nutritional quality of algal silage, the method comprising the steps of:
   capturing an amount of algal-microbial biomass and an amount of wastewater;
   disposing the amount of algal-microbial biomass and the amount of wastewater within a bioreactor;
   subjecting the amount of algal-microbial biomass and the amount of wastewater to electromagnetic radiation emitted from an electromagnetic generator via a slotted waveguide;
   via the electromagnetic radiation, uniformly heating the amount of algal-microbial biomass and the amount of water to a predetermined temperature, thereby converting at least a portion of the amount of algal-microbial biomass and the amount of wastewater into a microbial mat;
   annealing the microbial mat into a plurality of laminated structures, thereby inhibiting further microorganism growth within the microbial mat; and
   disposing the microbial mat on a surface of a body of water, such that the microbial mat is configured to serve as a feed source for aquaculture organisms disposed beneath the surface of the body of water.

2. The method of claim 1, wherein the slotted waveguide is a non-linear slotted waveguide.

3. The method of claim 2, further comprising the step of concentrating an amount of the electromagnetic radiation via an annealing area of the non-linear slotted waveguide in a direction toward the bioreactor.

4. The method of claim 1, wherein the electromagnetic radiation is microwave energy.

5. The method of claim 1, wherein the electromagnetic radiation is radiofrequency energy.

6. The method of claim 1, wherein the step of subjecting the amount of algal-microbial biomass and the amount of wastewater to electromagnetic radiation includes the step of emitting a plurality of doses of electromagnetic radiation from the electromagnetic generator, whereby subsequent to receiving at least one of the plurality of doses of electromagnetic radiation, the microbial mat is uniformly heated, thereby inhibiting microorganism growth within the microbial mat.

7. The method of claim 6, wherein the plurality of doses of electromagnetic radiation are emitted for approximately two hours per day for a period of between three and five days.

8. The method of claim 1, wherein the predetermined temperature is a temperature at which microorganism growth within the amount of algal-microbial biomass is inhibited.

9. A system for enhancing a nutritional quality of algal silage, the system comprising:
   a bioreactor containing algal-microbial biomass, wastewater, and a microbial mat containing an amount of the algal-microbial biomass and an amount of the wastewater;
   an electromagnetic generator disposed proximate to the bioreactor, the electromagnetic generator in mechanical communication with a slotted waveguide configured to emit electromagnetic radiation generated by the electromagnetic generator, wherein the slotted waveguide is a non-linear slotted waveguide;

wherein the electromagnetic generator is configured to emit electromagnetic radiation in a direction toward the bioreactor;

wherein the slotted waveguide further comprises an annealing area configured to concentrate an amount of the electromagnetic radiation in the direction toward the bioreactor; and wherein the bioreactor is configured to uniformly receive the emitted electromagnetic radiation, such that the microbial mat is uniformly subjected to the emitted electromagnetic radiation, and such that the microbial mat is annealed into a plurality of laminated structures that is configured to serve as a feed source for aquaculture organisms.

10. The system of claim 9, wherein the electromagnetic radiation is microwave energy.

11. The system of claim 9, wherein the electromagnetic radiation is radiofrequency energy.

12. The system of claim 9, further comprising the microbial mat being disposed on a surface of a body of water.

13. A method of enhancing a nutritional quality of algal silage, the method comprising the steps of:
capturing an amount of algal-microbial biomass and an amount of wastewater;
disposing the amount of algal-microbial biomass and the amount of wastewater within a bioreactor;
subjecting the amount of algal-microbial biomass and the amount of wastewater to electromagnetic radiation emitted from an electromagnetic generator via a non-linear slotted waveguide including an annealing area;
concentrating at least a portion of the electromagnetic radiation through the annealing area of the non-linear slotted waveguide in a direction toward the bioreactor;
via the electromagnetic radiation, uniformly heating the amount of algal-microbial biomass and the amount of water to a predetermined temperature, thereby converting at least a portion of the amount of algal-microbial biomass and the amount of wastewater into a microbial mat;
annealing the microbial mat into a plurality of laminated structures, thereby inhibiting further microorganism growth within the microbial mat; and
disposing the microbial mat on a surface of a body of water, such that the microbial mat is configured to serve as a feed source for aquaculture organisms disposed beneath the surface of the body of water.

14. The method of claim 13, wherein the electromagnetic radiation is microwave energy.

15. The method of claim 13, wherein the electromagnetic radiation is radiofrequency energy.

16. The method of claim 13, wherein the step of subjecting the amount of algal-microbial biomass and the amount of wastewater to electromagnetic radiation includes the step of emitting a plurality of doses of electromagnetic radiation from the electromagnetic generator, whereby subsequent to receiving at least one of the plurality of doses of electromagnetic radiation, the microbial mat is uniformly heated, thereby inhibiting microorganism growth within the microbial mat.

17. The method of claim 16, wherein the plurality of doses of electromagnetic radiation are emitted for approximately two hours per day for a period of between three and five days.

18. The method of claim 13, wherein the predetermined temperature is a temperature at which microorganism growth within the amount of algal-microbial biomass is inhibited.

* * * * *